United States Patent
Tolosa et al.

(10) Patent No.: US 9,883,823 B2
(45) Date of Patent: Feb. 6, 2018

(54) SYSTEM AND METHOD FOR DETERMINING AN IN VIVO CONCENTRATION OF A SMALL MOLECULE SUBSTANCE OF INTEREST IN A NONINVASIVE MANNER

(71) Applicants: Leah Tolosa, Columbia, MD (US);
Xudong Ge, Ellicott City, MD (US);
Yordan Kostov, Columbia, MD (US);
Michael Tolosa, Columbia, MD (US);
Govind Rao, Ellicott City, MD (US)

(72) Inventors: Leah Tolosa, Columbia, MD (US);
Xudong Ge, Ellicott City, MD (US);
Yordan Kostov, Columbia, MD (US);
Michael Tolosa, Columbia, MD (US);
Govind Rao, Ellicott City, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 1050 days.

(21) Appl. No.: 13/758,867

(22) Filed: Feb. 4, 2013

(65) Prior Publication Data
US 2013/0253295 A1 Sep. 26, 2013

Related U.S. Application Data

(60) Provisional application No. 61/594,514, filed on Feb. 3, 2012, provisional application No. 61/672,078, filed on Jul. 16, 2012.

(51) Int. Cl.
*A61B 5/00* (2006.01)
*A61B 5/145* (2006.01)
(Continued)

(52) U.S. Cl.
CPC ...... *A61B 5/14532* (2013.01); *A61B 10/0045* (2013.01); *B01L 3/5029* (2013.01);
(Continued)

(58) Field of Classification Search
CPC . A61B 5/150343; A61B 10/0045; A61B 5/15; B01L 3/5029
See application file for complete search history.

(56) References Cited

U.S. PATENT DOCUMENTS 5,139,023 A * 8/1992 Stanley ............. A61B 5/14532
600/368
5,458,140 A * 10/1995 Eppstein ............ A61B 5/14514
600/573
(Continued)

OTHER PUBLICATIONS

Huang et al., Noninvasive Glucose Monitoring by Back Diffusion via Skin: Chemical and Physical Enhancements, Biol. Pharm. Bull 26(7), Jul. 2003, p. 983-987.*

*Primary Examiner* — Puya Agahi
(74) *Attorney, Agent, or Firm* — Rene A. Vazquez, Esq.

(57) ABSTRACT

Systems and methods for determining an in vivo concentration of a small molecule substance of interest is provided that takes advantage of the semi-permeable nature of skin, which allows small molecules to passively diffuse through the skin and onto the skin surface. The systems and methods of the present invention allow for the collection of these small molecules that have passively diffused through the skin without skin disruption or breaking of the skin. The systems and methods of the present invention are noninvasive, painless and safe even for delicate newborns, and are particularly suited for the determination of blood glucose in newborns and infants in a noninvasive manner.

16 Claims, 14 Drawing Sheets

(51) Int. Cl.
  *A61B 10/00* (2006.01)
  *B01L 3/00* (2006.01)
  *G01N 33/542* (2006.01)
  *A61B 5/15* (2006.01)

(52) U.S. Cl.
  CPC .............. *G01N 33/542* (2013.01); *A61B 5/15* (2013.01); *A61B 5/150343* (2013.01); *B01L 2300/0663* (2013.01); *B01L 2300/0816* (2013.01)

(56) References Cited

U.S. PATENT DOCUMENTS

| | | | | |
|---|---|---|---|---|
| 5,817,012 | A * | 10/1998 | Schoendorfer | A61B 10/0035 600/362 |
| 2005/0215871 | A1* | 9/2005 | Feldman | A61B 5/14514 600/309 |
| 2006/0058602 | A1* | 3/2006 | Kwiatkowski | A61B 5/14514 600/407 |
| 2007/0027383 | A1* | 2/2007 | Peyser | A61B 5/14521 600/347 |
| 2007/0105176 | A1* | 5/2007 | Ibey | C12Q 1/54 435/14 |
| 2008/0261255 | A1* | 10/2008 | Tolosa | G01N 33/542 435/15 |

* cited by examiner

GLUCOSE BP

SYSTEM AND METHOD FOR DETERMINING AN IN VIVO CONCENTRATION OF A SMALL MOLECULE SUBSTANCE OF INTEREST IN A NONINVASIVE MANNER

This application also claims priority to U.S. Provisional Application Ser. No. 61/594,514, filed Feb. 3, 2012 and U.S. Provisional Application Ser. No. 61/672,078, filed on Jul. 16, 2012. The disclosures of both of these provisional applications are incorporated herein by reference in their entirety.

GOVERNMENT RIGHTS

This invention was made with government support under Grant No. R41HD069207 awarded by the National Institutes of Health. The government has certain rights in this invention.

BACKGROUND OF THE INVENTION

1. Field of the Invention

The present invention relates to the noninvasive detection and measurement of small molecule substances that have passively diffused through the skin such as, for example, the noninvasive detection and measurement of glucose that has passively diffused through the skin, and more specifically the extrapolation of in vivo concentrations of the small molecule substance based on the amount of the small molecule substance that has diffused through the skin.

2. Background of the Related Art

The standard of care for determining an in vivo concentration of a host of small molecule substances (e.g., glucose) is by sampling venous blood for analysis in the lab, or by sampling a small volume of blood from a prick on the skin for point-of-care (POC) devices. The former requires the ambulatory patient to visit the doctor's office or the lab for a phlebotomy. Results can take up to several days. The latter is exemplified by the commercial glucometer where the patient himself administers the test at home or the nurse administers the test on the patient by the hospital bedside. Results can be obtained almost immediately. In both cases, however, a break in the skin is necessary which results in varying degrees of discomfort as well as potential exposure to infections.

In low birth weight (LBW) infants, the adverse effects of these kinds of tests are even more exaggerated. Pain causes undue distress on infants resulting in not only short term but also long term consequences, such as the development of abnormal response to pain in some children. The inherent low blood volume of extremely LBW infants means multiple blood withdrawals could result in anemia or might require blood transfusions. The potential for exposure to infections is therefore magnified.

Glucose is the main energy source for a neonate to survive and develop normally. At birth, clamping the umbilical cord interrupts the continuous transplacental transfer of glucose and other nutrients, and the newborn infant must mobilize its surge in the levels of circulating epinephrine, norepinephrine, and glucagon and a fall in insulin levels. These hormones concomitantly mobilize hepatic glycogen and stimulate gluconeogenesis, resulting in a steady rate of glucose production and maintenance of the plasma glucose concentration. However, when stressors such as maternal diabetes, preterm birth, temperature stress and infection disrupt this delicate balance, hypoglycemia or hyperglycemia can result.

Both extremes of blood glucose in newborns pose significant challenges in the clinical management of the sick infant, requiring careful and vigilant monitoring to minimize impact on infant morbidity and mortality.

Hypoglycemia is the most common metabolic problem in neonates, occurring in as many as 5-15% of normal newborn infants and as high as 73% in the high-risk intrauterine growth restricted (IUGR)/small for gestational age (SGA) preterm infants. Although the absolute definition or value of hypoglycemia has been debated, most clinicians agree that serum glucose of less than 35-45 mg/dL defines neonatal hypoglycemia. Glucose is the primary energy substrate for the developing brain, therefore, it is imperative to monitor serum glucose frequently in the preterm population to promptly detect and treat neonatal hypoglycemia. Signs of hypoglycemia include hypotonia, bradycardia, hypothermia, lethargy, and poor feeding. However, the greatest concerns that can develop from significant, prolonged, and/or recurrent episodes of hypoglycemia are seizures and associated short and long-term neurodevelopmental impairments or death.

Hyperglycemia is less frequently observed in full term newborn infants than hypoglycemia, but is the most commonly observed perturbation of glucose metabolism in low birth weight (LBW) infants in the neonatal intensive care units (NICUs). Among extremely low birth weight (ELBW) infants, the incidence of neonatal hyperglycemia is estimated to be 45-80%. Like hypoglycemia, the exact definition in newborns remains unclear. However, a serum glucose level >125 mg/dL in term infants and >150 mg/dL in preterm infants can be considered hyperglycemic.

Because hyperglycemia is also associated with increased neonatal morbidity and mortality, this condition needs to be closely and carefully monitored. Hyperglycemia increases blood osmolarity and may cause electrolyte disturbances, osmotic diuresis, and the associated loss of electrolytes in the urine and has been associated with retinopathy of prematurity (ROP) and intra-ventricular hemorrhage (IVH). In addition, hyperglycemia also causes alterations in the immune response in the already immune-compromised premature infants. In certain circumstances, insulin therapy may have to be initiated in a hyperglycemic infant, at which point that infant would require more frequent glucose testing to monitor therapy and to prevent hypoglycemia.

The current standard of care for determining glucose levels from an infant is either by a point of care testing (POCT) bedside glucose analyzer and/or with one of the laboratory enzymatic methods. In either situation, the infant would have to be subjected to painful and invasive blood sampling, either from an arterial/venous draw or a heel lance to obtain the blood for testing. Premature infants who are already immune-compromised from an immature immune system are placed at greater risk of developing infections from either the blood draw process, by breakage of the skin, or from transfusion-acquired infections since blood sampling often necessitates blood transfusions to correct the anemia. Furthermore, subjecting these infants to painful procedures show that such procedures alter the pain perception of the infants long-term with long-term outcomes. Therefore, a non-invasive method for monitoring glucose would be a break-through in the medical management of sick, premature infants who are currently subjected to multiple blood draws.

Another problem is that currently available glucose analyzers were developed for adults. Less than 70 mg/dl blood glucose is considered hypoglycemic in adults, while in neonates it is <35 to 45 mg/dl. Thus, the limits by which clinical decisions need to be made for neonates are generally at the limits of accuracy and sensitivity of these analyzers. What may be considered acceptable sensor sensitivity for adults could overlook at risk neonates, leading to adverse consequences. Additionally, some of these glucose analyzers suffer from interference from the high oxygen, high bilirubin and high hemoglobin levels common in preterm infants. Thus, there are challenges on multiple fronts to designing an appropriate glucose sensor for neonates.

SUMMARY OF THE INVENTION

An object of the invention is to solve at least the above problems and/or disadvantages and to provide at least the advantages described hereinafter.

Therefore, an object of the present invention is to provide a method for determining an in vivo concentration of a small molecule substance of interest in a subject based on an amount of the small molecule substance of interest that passively diffuses through the skin of the subject.

Another object of the present invention is to provide a method for determining blood glucose in a subject in a noninvasive way.

Another object of the present invention is to provide a method for determining blood glucose in a subject based on an amount of glucose that passively diffuses through the skin of the subject.

Another object of the present invention is to provide a glucose detection system and method that is sensitive enough to measure the concentration of glucose that passively diffuses through the skin of a subject.

Another object of the present invention is to provide a system and method for collecting glucose from the skin of a subject.

To achieve at least the above objects, in whole or in part, there is provided a method of determining an in vivo concentration of a small molecule substance of interest in a subject, wherein the small molecule substance of interest has a molecular size that is capable of passively diffusing through the skin of the subject, the method comprising placing a collector for the small molecule substance of interest in contact with an area of the skin of the subject, maintaining the collector in contact with the skin area for a predetermined time that is sufficient to collect at least some of the small molecule substance of interest that has passively diffused through the skin, measuring a concentration of the small molecule substance of interest collected by the collector, and extrapolating an in vivo concentration of the small molecule substance of interest based on the measured concentration of the small molecule substance of interest that passively diffused through the skin and that was collected by the collector.

To achieve at least the above objects, in whole or in part, there is also provided a method of determining blood glucose in a subject, comprising placing a glucose collector in contact with an area of the skin of the subject, wherein the glucose collector is adapted to collect glucose that has passively diffused through the skin of the subject ("skin glucose"), maintaining the glucose collector in contact with the skin area for a predetermined time that is sufficient to collect at least some of the skin glucose, measuring a concentration of the skin glucose collected by the glucose collector, and extrapolating blood glucose concentration in the subject based on the measured skin glucose concentration.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The present invention takes advantage of the semi-permeable nature of skin, which allows small molecules to passively diffuse through the skin and onto the skin surface. The systems and methods of the present invention allow for the collection of these small molecules on the skin without skin disruption or breaking of the skin. Further, active disturbance of skin permeability, such as by the application of an electric current or ultrasound, is not required. The systems and methods of the present invention are noninvasive, painless and safe even for delicate newborns.

Additionally, the systems and methods of the present invention are especially suited for the thin, underdeveloped skin of neonates that allow diffusion of small molecules more readily than adult skin. Examples of substances that can be collected with these methods are glucose, lactate, and other metabolites, amino acids, sodium ions, calcium, etc. Whether in adults, neonates or other mammals, highly sensitive and highly specific sensors and analytical methods are necessary because of the low levels of molecules that can diffuse through the skin. As will be discussed in more detail below, suitable sensors include, but are not limited to, binding protein biosensors, high performance liquid chromatography (HPLC) with electrochemical detection and atomic absorption spectroscopy.

Figure 1:
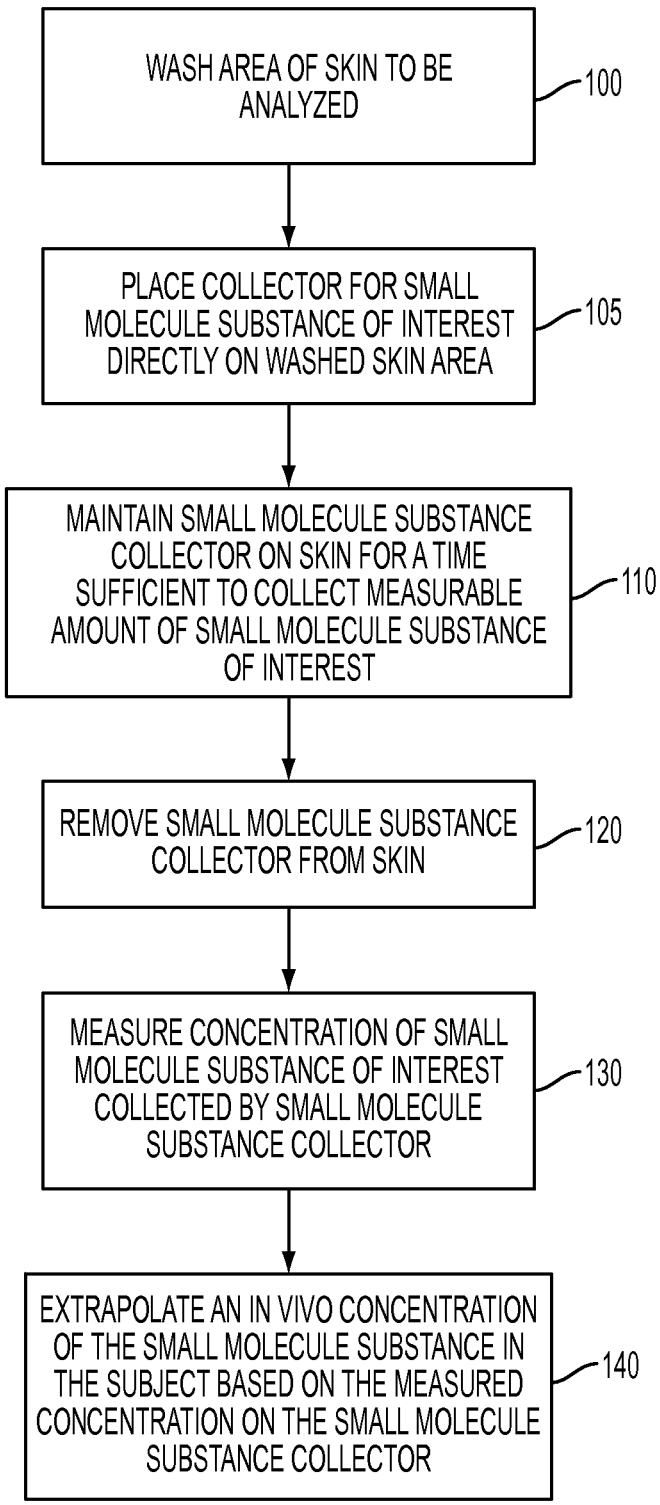
FIG. 1 is a flow chart of a generalized method for determining an in vivo concentration of a small molecule substance of interest by collecting and measuring the small molecule substance that has passively diffused through the skin of the subject, in accordance with one embodiment the present invention.

FIG. 1 is a flow chart of a generalized method for determining an in vivo concentration of a small molecule substance of interest, such as glucose, by collecting and measuring the small molecule substance that has passively diffused through the skin of the subject, in accordance with one embodiment the present invention. The phrase "in vivo," as used herein, refers to inside the body of the subject. The phrase "small molecule substance", as used herein, refers to a substance whose molecules are small enough to passively diffuse through skin of a subject. In addition to glucose, other small molecule substances of interest can include, but are not limited to, lactate, and other metabolites, amino acids, sodium ions and calcium. Further, although the present invention is described in the context of human subjects, it should be appreciated that the present invention can be used to determine the in vivo concentration of a small molecule substance of interest in any mammal. Thus, the term "subject," as used herein, refers to any mammal.

The method starts at step 100, where the skin area to be analyzed is preferably washed. This washing step is optional, but it is recommended in order to remove any small molecule substance of interest that may have accumulated on the skin over time. The solution used to wash the skin area is preferably the same solution that is used for the collector (step 105). The skin area is preferably washed for a time sufficient to remove any accumulated small molecule substance of interest. The wash time can vary from subject to subject, but a wash time of between 5 and 15 minutes should be sufficient for most subjects.

The method then proceeds to step 105, where a collector for the small molecule substance of interest is placed directly on the washed skin area. The collector is preferably a solution, suitably a buffer solution, distilled water or deionized water, that is applied directly to the skin area of the subject. Examples of buffer solutions that can be used include, but are not limited to, phosphate buffered saline (PBS), carbonate buffer, acetate buffer and TRIS buffer. If the small molecule substance of interest is sodium or potassium, the preferred collector is deionized water. If the small molecule substance of interest is glucose, the preferred collector is PBS.

Alternatively, the collector can be a swab made from a material that is absorbent to the small molecule substance of interest and that is pre-moistened with a buffer solution, distilled water or deionized water. In the case of a swab, the swab is pressed against the washed skin area of the subject. If the small molecule substance of interest is sodium or potassium, the swab is preferably pre-moistened with deionized water. If the small molecule substance of interest is glucose, the swab is preferably pre-moistened with PBS.

At step 110, the small molecule substance collector is maintained in contact with the skin for a time sufficient to collect at least some of the small molecule substance of interest that has diffused through the skin. If a solution or swab is used to collect the small molecule substance of interest, agitation of the skin may optionally be used to help dissolve the small molecule substance of interest into the solution or swab. The time that the collector is maintained in contact with the skin (collection time) can vary from subject to subject, but a collection time of between 1 and 5 minutes should be sufficient for most subjects.

Next, at step 120, the small molecule substance collector is removed from the skin. In the case of a solution, the solution is collected from the skin of the subject. In the case of a swab, the swab is removed from the skin surface. Then, at step 130, a detector is used to measure the small molecule substance of interest collected by the small molecule substance collector. The type of detector used will depend on the small molecule substance of interest, as will be explained in more detail below. The detector must be sufficiently sensitive to detect the relatively small concentrations of the small molecule of interest that will be present in the small molecule substance collector. Suitable sensors include, but are not limited to, binding protein biosensors, high performance liquid chromatography (HPLC) with electrochemical detection and atomic absorption spectroscopy.

At step 140, the in vivo concentration of the small molecule substance of interest in the subject is extrapolated based on the concentration of the small molecule substance of interest in the small molecule substance collector. In order to extrapolate the in vivo concentration of the small molecule substance of interest, the method must be calibrated by determining the correlation between the in vivo concentration of the small molecule substance of interest and the concentration of the small molecule substance of interest in the small molecule substance collector, as will be explained in more detail below.

By way of example, the present invention will now be described in connection with the noninvasive monitoring of blood glucose in infants by detecting and measuring glucose that has diffused through the skin and onto the skin surface. However, as explained above, it should be appreciated that the present invention can be used to monitor the in vivo concentration of any type of small molecule substance by detecting and measuring the small molecule substance that has diffused through the skin.

Figure 2:
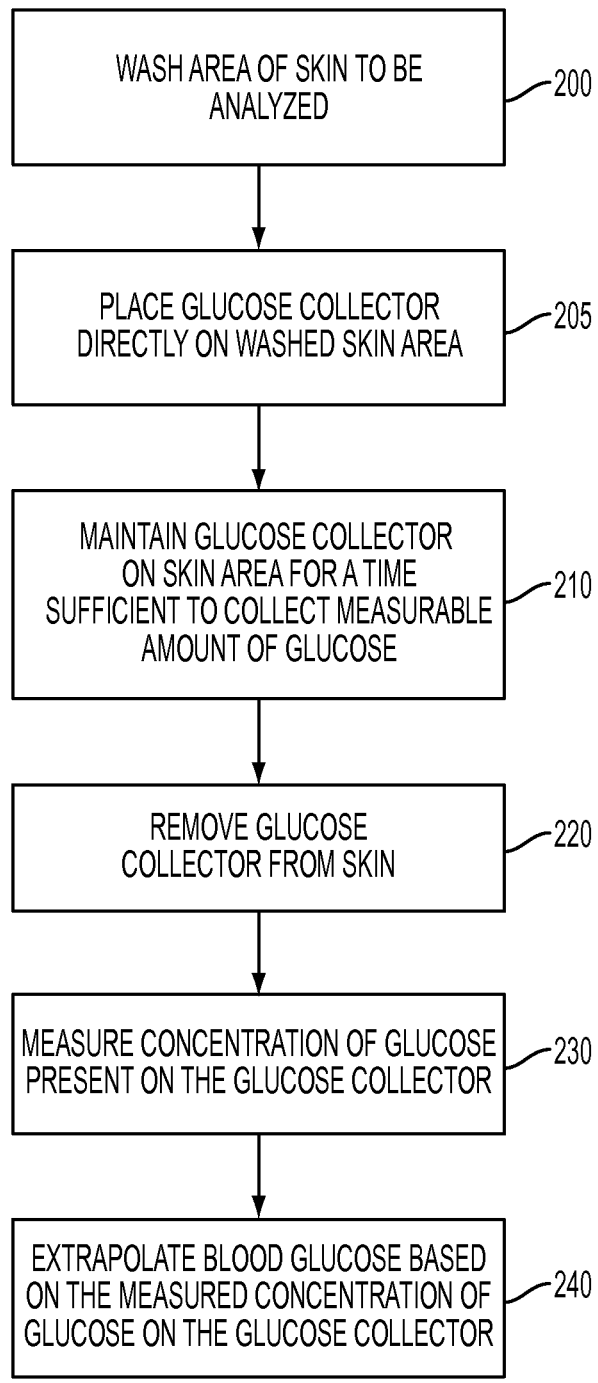
FIG. 2 is a is a flow chart of a method for determining blood glucose concentration by collecting and measuring the glucose that has passively diffused through the skin of the subject, in accordance with one embodiment of the present invention.

FIG. 2 is a flow chart of a method for determining blood glucose concentration by collecting and measuring the glucose that has passively diffused through the skin of the subject, in accordance with one embodiment the present invention. The method starts at step 200, where the skin area to be analyzed is preferably washed. As discussed above, this washing step is optional, but it is recommended in order to remove any glucose that may have accumulated on the skin over time. As discussed above, the solution used to wash the skin area is preferably the same solution that is used for the collector (step 205). The skin area is preferably washed for a time sufficient to remove any accumulated small molecule substance of interest. The wash time can vary from subject to subject, but a wash time of between 5 and 15 minutes should be sufficient for most subjects.

The method then proceeds to step 205, where a glucose collector is placed directly on the skin of a subject. The glucose collector is preferably a solution, suitably a buffer solution, distilled water or deionized water, that is applied directly to the skin of the subject. The preferred glucose collector is a buffer solution. Examples of buffer solutions that can be used include, but are not limited to, phosphate buffered saline (PBS), carbonate buffer, acetate buffer and TRIS buffer.

Alternatively, the collector can be a swab made from a material that is absorbent to glucose, suitably filter paper that has been pre-moistened with a buffer solution, distilled water or deionized water (preferably PBS). In the case of a swab, the swab is pressed against the washed skin area of the subject. Preferred glucose detectors will be discussed in more detail below.

At step 210, the glucose collector is maintained in contact with the skin area for a time sufficient to collect at least some of the glucose present on the skin. If a solution or swab is used to collect the glucose, agitation of the skin may optionally be used to help dissolve the glucose into the buffer solution or swab. The time that the glucose collector is maintained in contact with the skin (collection time) can vary from subject to subject, but a collection time of between 1 and 5 minutes should be sufficient for most subjects.

Next, at step 220, the glucose collector is removed from the skin. In the case of a solution, the solution is collected from the skin of the subject. In the case of a swab, the swab is removed from the skin surface. Then, at step 230, a detector is used to measure the glucose collected by the glucose collector. The detector must be sufficiently sensitive to detect the relatively small concentrations of glucose that will be present in the glucose collector. In a preferred embodiment, the detector preferably utilizes a glucose binding protein sensor, as will be explained in more detail below.

At step 240, blood glucose in the subject is extrapolated based on the concentration of glucose on the glucose collector. In order to extrapolate blood glucose, the method must be calibrated by determining the correlation between blood glucose and the concentration of glucose on the glucose collector, as will be explained in more detail below.

The Permeability of Neonatal Skin

Because neonatal skin is underdeveloped, its cutaneous barrier is more permeable than mature skin. This permeability is a function of gestational and postnatal age and can be measured as the transepidermal water loss (TEWL). TEWL is related to the post-conceptional age (PCA) as follows: $TEWL=3.3+41\times e^{-0.026(PCA-160)}$. Many investigators have looked at this increased permeability as a potential noninvasive route for the delivery of drugs to sick neonates. Passive diffusion and technologies such as iontophoresis have been investigated in the transfer of drugs through the thin cutaneous barrier.

Additionally, differentially tape-stripped porcine skin was developed and validated as an in vitro model for these drug delivery studies. Attempts have also been made to monitor drugs that are already in the neonates' system through reverse iontophoresis. It is apparent from the latter that for neutral molecules, reverse iontophoresis is no better than passive diffusion through the skin. While this is not a desirable outcome for drug monitoring, it is of particular significance for monitoring neutral small molecules like glucose that could easily diffuse out of the skin together with TEWL. The amount of glucose that diffuses out of the skin is much less than the glucose in the blood, which is why the detector for measuring the glucose concentration on the glucose collector preferably utilizes a glucose binding protein sensor.

Glucose Collectors

Figure 3:
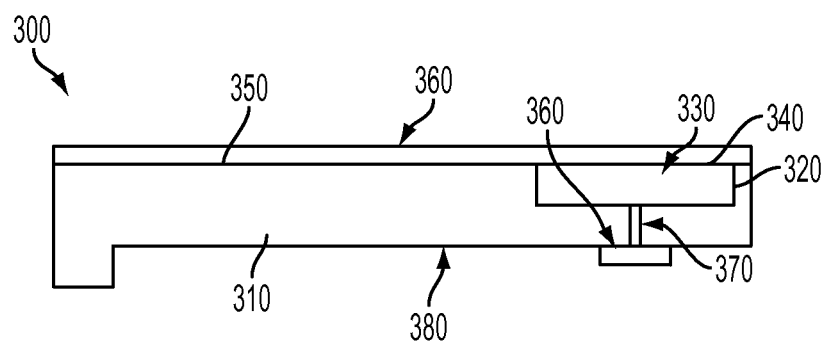
FIG. 3 is a side view of a swab 300 designed to collect glucose present on the skin of a subject, in accordance with one embodiment of the present invention.

FIG. 3 is a side view of a swab 300 designed to collect glucose present on the skin of a subject, in accordance with one embodiment of the present invention. The swab 300 includes a housing 310 with a recess 320 in which a glucose absorbent material, preferably highly absorbent cellulose filter paper 330, is placed. The housing 310 is preferably made of pliable plastic.

The filter paper 330 has a preferable thickness of approximately 1 mm. The filter paper is preferably held in place in the recess 320 by an adhesive or by mechanical means using a clip or by friction between the filter paper and the recess 320. Although filter paper 330 is one preferred option for the glucose absorbent material, any material that is glucose absorbent can be used in place of the filter paper 330. The depth of the recess 320 is preferably made so that when the filter paper 330 is seated in the recess 320, a contact surface 340 of the filter paper 330 is substantially flush with a front surface 350 of the housing 310.

The filter paper 330 is preferably pre-moistened with a buffer solution, distilled water or deionized water. A pin hole or opening 370 can be optionally made in the housing 310 that extends from a back surface 380 of the housing 310 to the recess 320. The pin hole 370 aids in the absorption of glucose onto the filter paper 330. Adhesive tape 360 can be optionally applied to the front and back surfaces 350 and 380 of the housing, so as to cover the filter paper 330 and the pin hole 370. The adhesive tape 360 keeps the pre-moistened filter paper 330 moist and sterile prior to use.

Figure 4:
FIG. 4 is a perspective view showing how the swab of FIG. 3 is used.

As shown in FIG. 4, to use the swab 300, the adhesive tape 360, if used, is removed. The front surface 350 of the swab 300 is then pressed onto the surface of the skin 390 such that the contact surface 340 of the filter paper 330 is in contact with the skin 390. This is done for a predetermined period of time ("collection time") that will allow the glucose present on the skin 390 to be absorbed into the filter paper 330. The collection time is determined during calibration of the method, as will be explained in more detail below. Although FIG. 4 shows the swab being pressed against the skin of the leg, the swab can be pressed against any part of the skin (e.g., the stomach, arm, back, etc.).

After the collection time has passed, the filter paper 330 is preferably submerged in a solution, preferably phosphate buffered saline ("PBS"), so as to allow the glucose present in the filter paper 330 to diffuse into the solution. Although the preferred solution is PBS, distilled water or deionized water may also be used.

Figure 5A:
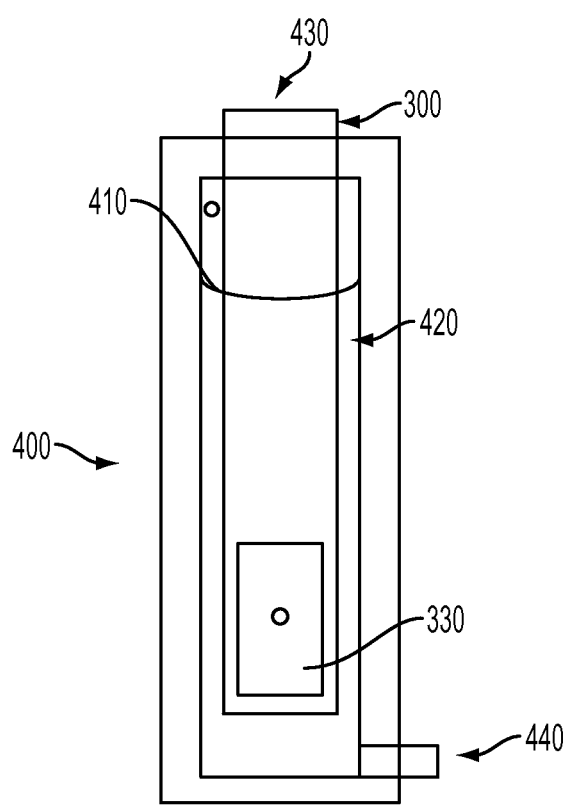
FIGS. 5A and 5B are front and side perspective views, respectively, of a vessel used to submerge the filter paper shown in FIG. 3 in a buffer solution, in accordance with one preferred embodiment of the present invention.
Figure 5B:
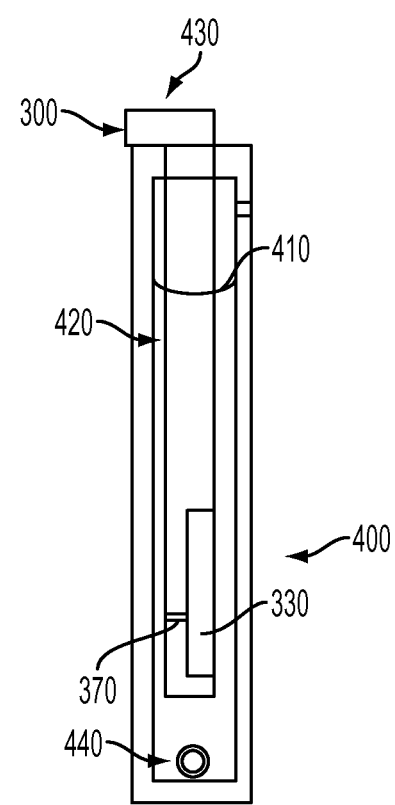

FIGS. 5A and 5B are perspective views of a vessel 400 used to submerge the filter paper 330 in a solution 410, in accordance with one preferred embodiment of the present invention. FIG. 5A is a front view and FIG. 5B is a side view of the vessel 400. The vessel 400 is preferably made of plastic and is designed to hold a volume of solution 410 in a reservoir 420. The reservoir 420 is also designed to receive the swab 300.

The swab 300 is placed in the reservoir 420 such that the filter paper 330 is submerged in the solution 410. A bottom end 430 of the swab 300 is preferably shaped to form a lip that can be used to hang the swab 300 on a wall of the vessel 400 such that the filter paper 330 is submerged in the solution 410. A flexible septum 440, suitably a rubber septum, is preferably positioned at the bottom of the reservoir 420 for withdrawing a sample of the solution 410 with a syringe.

As discussed above, the filter paper 330 is submerged in the buffer solution 410 for a sufficient time as to allow the glucose absorbed into the filter paper 330 to diffuse into the buffer solution 410. In order to facilitate the diffusion of glucose from the filter paper 330 to the buffer solution 410, the vessel 400 with the buffer solution 410 and the swab 300 inserted into the reservoir 420 can optionally be shaken in a sonicator (not shown).

A sample of the solution 410, which now contains glucose that diffused out from the filter paper 330, is then removed from the reservoir 420, preferably with a syringe through the rubber septum 440, and is analyzed with a sensitive glucose detector to determine the glucose concentration in the sample. The concentration of blood glucose in the subject is then extrapolated based on the concentration of glucose in the buffer sample ("skin glucose").

The sampling protocol using the swab 300 can be optimized by using standard glucose solutions representing a range of glucose concentrations that can be applied as thin films on glass slides and allowed to dry, or applied as a thin film on the skin of subject. The varying concentrations of glucose on the slides or the skin are then analyzed using the swab 300, vessel 400 and glucose detector, as described above. The time over which the swab 300 is pressed against the glass slide or skin, as well as the time the glucose infused filter paper 330 is soaked in the solution 410 is then varied to find the optimal swab 300 application time and filter paper 300 soaking time.

Figure 6:
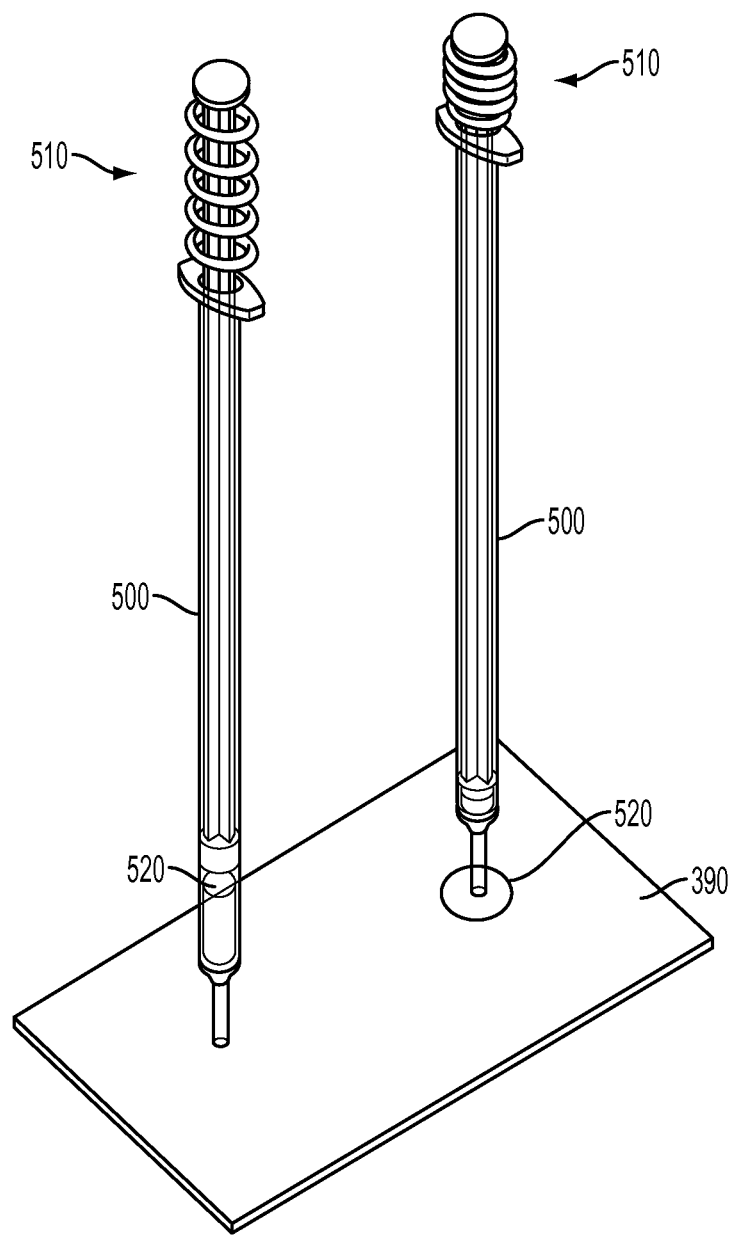
FIG. 6 is a perspective view of a glucose collection technique, in accordance with one embodiment of the present invention.

FIG. 6 is a perspective view of another glucose collection technique, in accordance with one embodiment of the present invention. The technique involves the use of a syringe 500 equipped with a return spring 510. The syringe 500 is used to dispense solution 520 onto the skin 390, as well as collect the solution 520 from the skin 390. FIG. 6 shows the syringe 500 dispensing the solution 520 onto the skin 390 (the syringe image on the right) and also shows the syringe 500 withdrawing the solution 520 from the skin 390 (the syringe image on the left).

In operation, the solution 520 is repeatedly dispensed onto the skin 390 and collected in order to effectively "wash" the skin area with the solution 520. The "washing" of the skin area with the solution 520 results in the removal of glucose present on the skin 390. That glucose ends up in the solution 520. After the "washing" process, the solution, which now contains glucose that was removed from the skin 390, is analyzed with a sensitive glucose detector, and blood glucose levels are extrapolated based on the skin glucose measured by the sensitive glucose detector. The preferred solution 520 is PBS, however, other buffer solutions, distilled water or deionized water may also be used.

Figure 7:
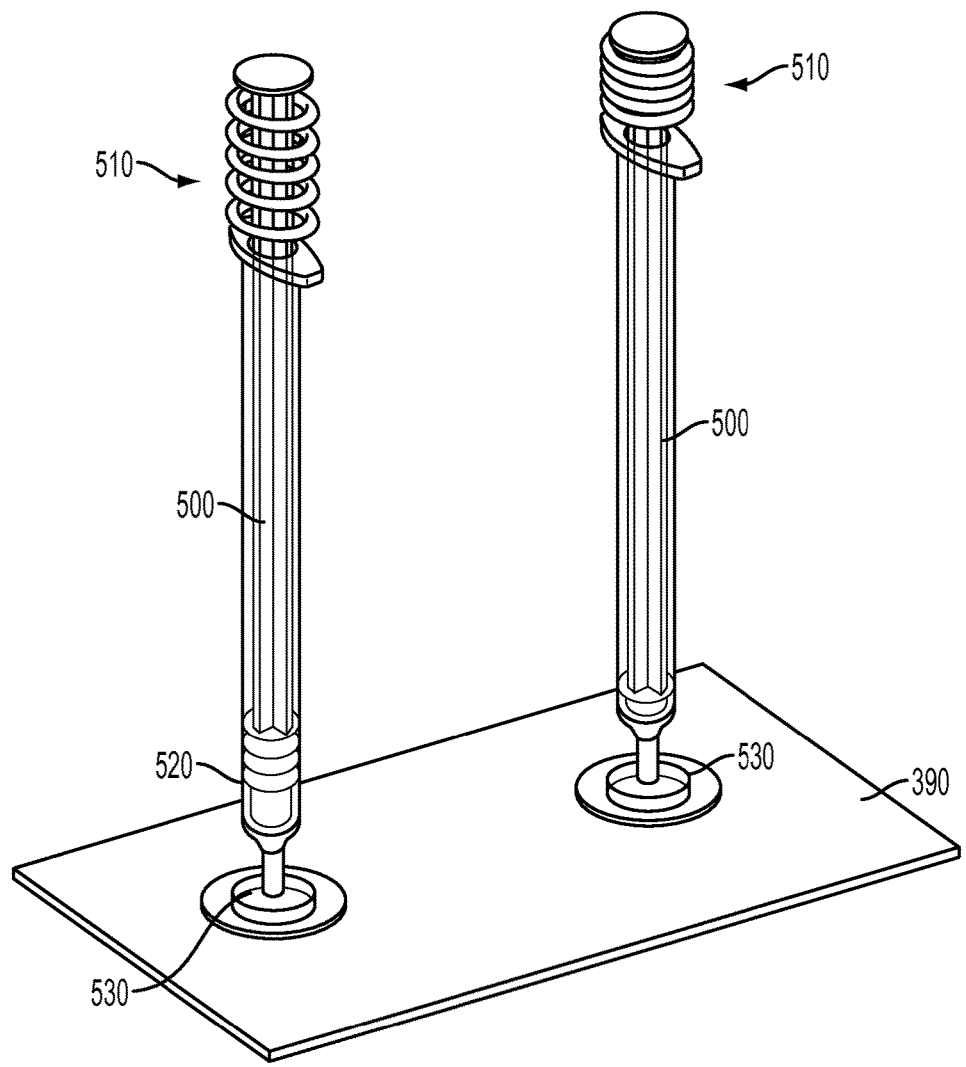
FIG. 7 is a perspective view of another glucose collection technique, in accordance with one embodiment of the present invention.

FIG. 7 is a perspective view of a glucose collection technique similar to the technique illustrated in FIG. 6, except that a rubber cup 530 is used to better contain the solution 520 when it is dispensed onto the skin 390. The rubber cup 530 is adapted to connect with the tip of the syringe 500, and is applied to the skin 390 of the subject. The solution 520 is repeatedly dispensed and collected as described above in connection with FIG. 6. The only difference is that it is dispensed into and collected from the rubber cup 530. When the solution 520 is dispensed into the rubber cup 530, it comes into contact with the skin 390.

Figure 8:
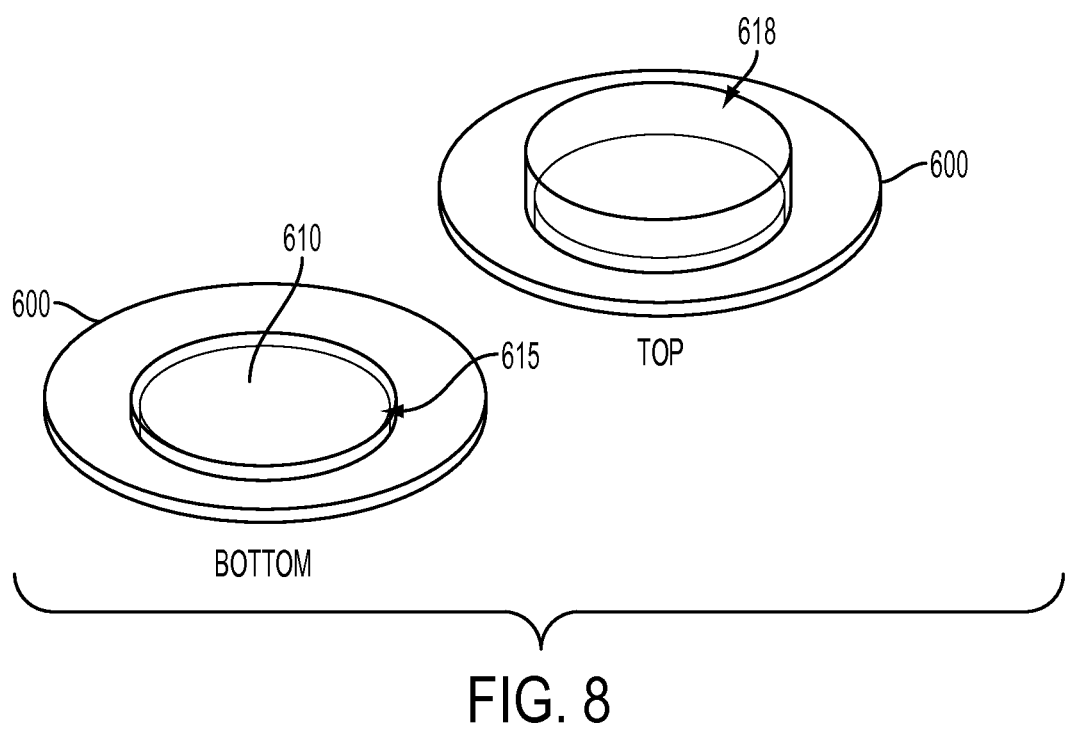
FIG. 8 shows top and bottom perspective views of a flexible rubber "blister" that can be used as a glucose collector, in accordance with one embodiment of the present invention.

FIG. 8 shows top and bottom perspective views of a flexible rubber "blister" 600 that can be used as a glucose collector, in accordance with one embodiment of the present invention. The solution 610 is pre-packaged in the rubber blister 600. The solution 610 may be held in place by a covering membrane (not shown) that is removed prior to use. To use, the covering membrane is removed and the blister 600 is applied to the skin 390 with the opening 615 face down so that the solution 610 contacts the skin. The top 618 of the blister 600 is then preferably massaged to create a "washing" effect on the skin 390.

Alternatively, the solution 610 may be loaded into the blister 600 by means of a syringe or other fluid dispenser. After glucose collection, the blister 600 is turned over to collect the solution 610. A cap (not shown) may be used to cover the blister to prevent fluid spillage/evaporation.

Glucose Detector

As discussed above, the glucose detector used to measure skin glucose must be very sensitive to detect the relatively low levels of glucose that diffuse through the skin. Accordingly, the glucose detector preferably utilizes a glucose binding protein (GBP) sensor, such as, for example, the GBP sensors described in U.S. Pat. Nos. 6,197,534, 7,718,353, 7,064,103, Ge, X., Tolosa, L., Rao, G., "Dual-labeled glucose binding protein for ratiometric measurements of glucose," Anal. Chem., 76 1403-1410 (2004), and Ge, X., Tolosa, L., Simpson, J., Rao, G., "Genetically engineered binding proteins as biosensors for fermentation and cell culture," Biotech. Bioeng., 84 723-721 (2003), which are all incorporated herein by reference in their entirety.

Figure 9:
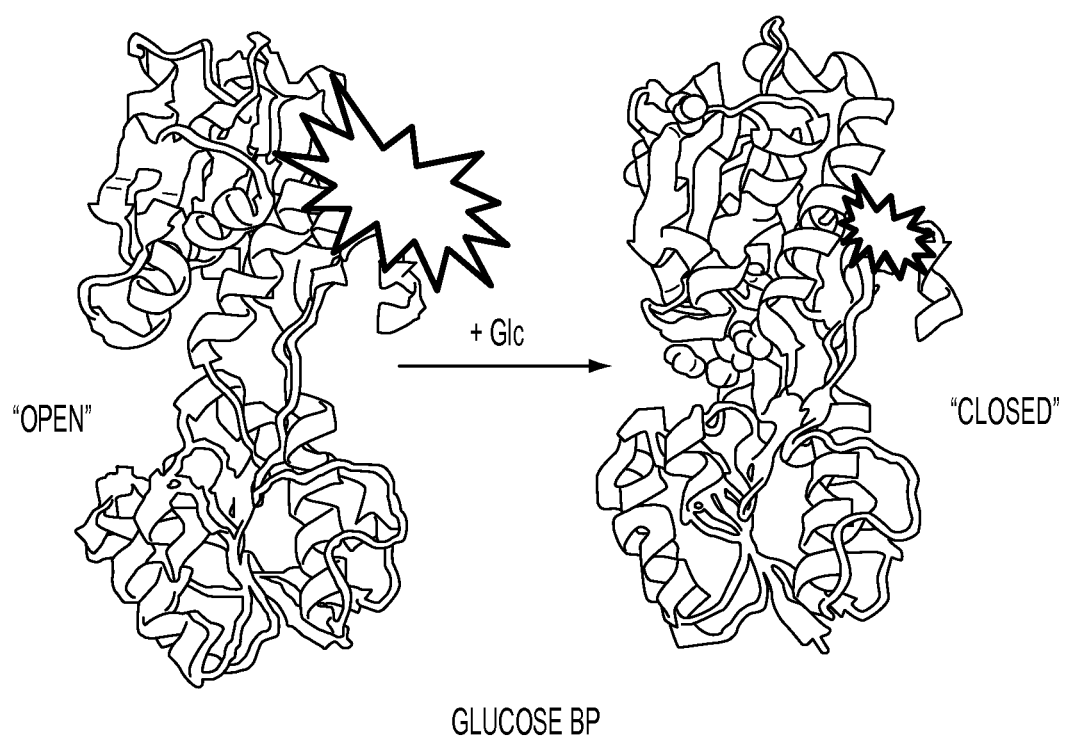
FIG. 9 is a schematic diagram of a glucose binding protein.

The GBP used is preferably the GBP found in the periplasmic space of gram negative bacteria. The GBP is not an enzyme and signal transduction is effected through the change in conformation of the protein upon binding of glucose, as shown in FIG. 9. We have taken advantage of this change in protein conformation by strategically introducing a cysteine mutation at position 255 and labeling that mutation with the polarity sensitive dye, acrylodan.

Figure 10:
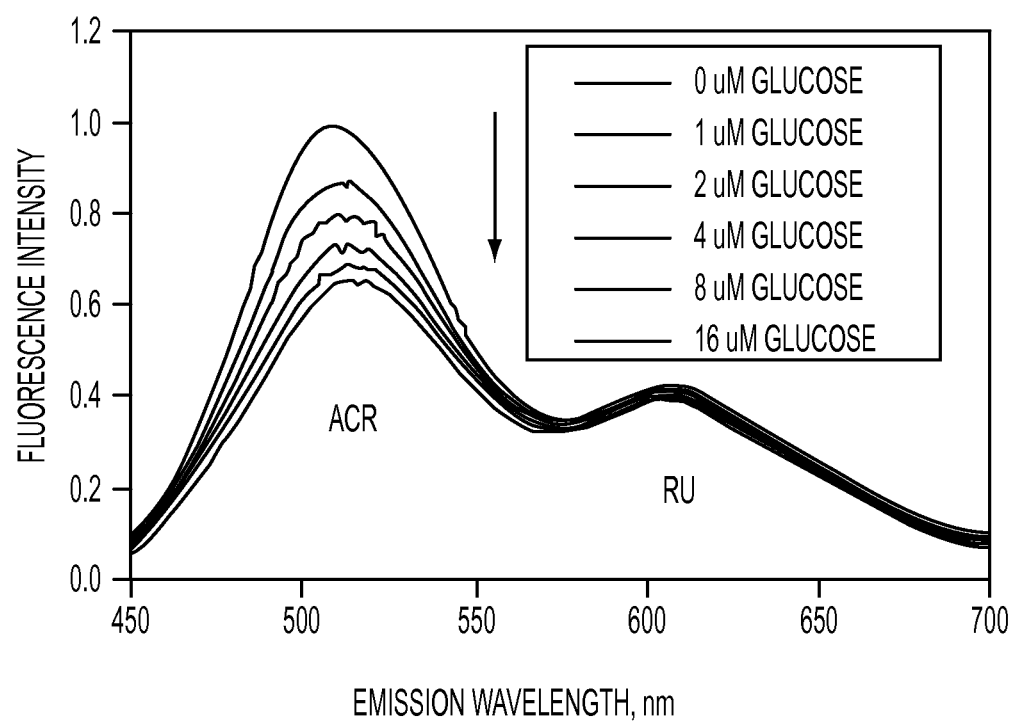
FIG. 10 is a plot of the fluorescence response of dye-labeled GBP as a function of glucose concentration.

Changes in fluorescence properties of the dye are then correlated to the concentration of the analyte in the sample, as shown in FIG. 10, which is a plot of the fluorescence response of dye-labeled GBP as a function of glucose concentration. This method of signal transduction has been demonstrated for several binding proteins for biosensing applications as a broad class of reagentless biosensors. The photophysical properties of the labeled proteins are tailored to complement the engineering of a low cost optical device, while maintaining sensitivity, accuracy and miniaturizability, as discussed in Lam, H., Rao G., Tolosa, L, "Low-Cost Optical Lifetime Assisted Ratiometric Glutamine Sensor Based on Glutamine Binding Protein," Anal. Biochem. 383, 61-67 (2008), Ge X., Lam H. T, Swati, M. J., LaCourse W. R., Rao G. and Tolosa L., "Comparing the Performance of the Optical Glucose Assay Based on the Glucose Binding Protein with High Performance Anion-exchange Chromatography with Pulsed Electrochemical Detection: Efforts to Design a Low-Cost Point-of-Care Glucose Sensor," J. Diabetes Science and Technology, 1(6) 864-872 (2007), and Lam H, Kostov Y, Rao G and Tolosa L, "A Luminescence Lifetime Assisted Ratiometric Fluorimeter for Biological Applications," Rev. Sci. Instruments, 80, 124302 (2009), which are all incorporated herein by reference in their entirety.

In contrast, commercially available test strip glucometers and glucose analyzers use glucose oxidase as the recognition element for glucose. This enzyme reacts with glucose and $O_2$ to form hydrogen peroxide, which is then detected either colorimetrically or by an electrode. The sensitivity of glucose oxidase is in the mM range and may be ineffective in detecting hypoglycemia. Further, the mM sensitivity may be too low to detect the small amount of glucose that permeates through neonatal skin. The major difference between the glucose oxidase biosensor and the preferred GBP sensor is that the GBP sensor is sensitive in the μM range. The high sensitivity and selectivity of GBP address limitations associated with current commercially available glucometers, including: (1) the need to withdraw a sample of blood through a break in the skin; (2) the limited number of tests that can be done because of this; and (3) the difficulty in detecting hypoglycemia, particularly in neonates. In contrast, the GBP sensor allows for: (1) accurately detecting the very small amounts of glucose that permeates through the thin neonate skin; (2) doing away with extracting blood through a break in the skin; (3) the possibility of more frequent glucose testing; and (4) potentially monitoring glucose continuously.

The dye-labeled GBP that generated the fluorescence response shown in FIG. 10 was labeled with with acrylodan in the S255C position, which can be observed as the peak centered at ~520 nm. This emission peak responds to increasing glucose concentrations as shown by the decreasing fluorescence intensity. A second dye, a ruthenium metal ligand complex (Ru) was attached to the N-terminal of the protein as a reference, allowing for more reliable ratiometric measurements. Ru (emission maximum at 620 nm) is a good reference because it is not influenced by the protein conformational changes and its fluorescence lifetime is ~200 times longer than acrylodan. This innovative choice of ratiometric dye pairs is the basis for lifetime assisted ratiometric sensing (LARS) and is meant to simplify the optoelectronic design of the stand alone device by decreasing the number of necessary parts, which in turn leads to miniaturization, while increasing the signal to noise ratio and lowering the cost of the final instrument. In another preferred embodiment of LARS, a europium metal ligand complex (Eu) can be used, which is also unaffected by protein conformational changes and has a lifetime that is ~70,000 times that of acrylodan. The longer-lived europium complex allows the optoelectronics to operate at much lower and more accessible modulation frequencies (i.e., at 10 kHz for Eu vs. 2 MHz for Ru). Accordingly, the electronic components operating at the lower frequency outperform the high speed components in terms of noise stability and cost.

The GBP sensor labeled with Acrylodan and either Eu or Ru is preferably immobilized on 50-175 μm Sepharose beads. These beads are available commercially with various functional groups using standard chemical reactions for immobilization of proteins. The GBP beads are then preferably confined in microfabricated wells, suitably etched using a $CO_2$ laser cutter. Calibration of the GBP beads can be done upon manufacture and given a code number. The user can then enter this code number into a point of care device which is pre-programmed to calculate the glucose concentrations from this code. Swabs with pre-determined glucose concentrations can also be provided to users as a reference. This will eliminate the need to do wet chemistry calibrations at the point of care and ensure a user-friendly device.

As discussed above, the GBP sensor are doubly labeled with acrylodan (emission max=~520 nm) as the signal transducing dye, and either Eu (emission max=~625 nm) or Ru (emission max=~620 nm) as the reference. The rationale for the reference dye (either Eu or Ru) is to provide a reference emission to correct for systematic errors that can affect the fluorescence intensity of acrydolan but are not associated with changes in glucose concentrations. Thus, the ratio of fluorescence signals from acrylodan and ruthenium increases the robustness of the data.

The most difficult task in developing devices for fluorescence ratiometric sensing is the isolation of signals when there is considerable overlap between the emission wavelengths of the two dyes. Conventionally, wavelength discrimination is achieved by using monochromators or bandpass filters. But these often eliminate a large portion of the emission light, leading to decreased signal intensities. Accordingly, an optical fluorimeter based on luminescence lifetime assisted ratiometric sensing (LARS) is used with the GBP sensor. The most significant innovation of LARS is the ability to discriminate between two overlapping luminescence signals based on differences in their luminescence decay rates.

A more detailed discussion of LARS can be found in Lam H, Kostov Y, Rao G and Tolosa L, "A Luminescence Lifetime Assisted Ratiometric Fluorimeter for Biological Applications", Rev. Sci. Instruments, 80, 124302 (2009), which is incorporated herein by reference in its entirety. Briefly, the intensity of the LED light source is modulated at two distinct frequencies as it illuminates the GBP sensor. When the GBP sensor has a mixture of "short" and "long"-lived fluorophores, one can choose two modulation frequencies where at the lower frequency the emission is the total of the fractional intensities of the two fluorophores, and in the higher frequency only the emission of the "short-lived" fluorophore is observed. In GBP sensors, only the "short-lived" fluorophore (acrylodan) is affected by the analyte (glucose). Thus, the ratio of the emission at the two selected frequencies can then be correlated to the analyte concentrations.

Figure 11:
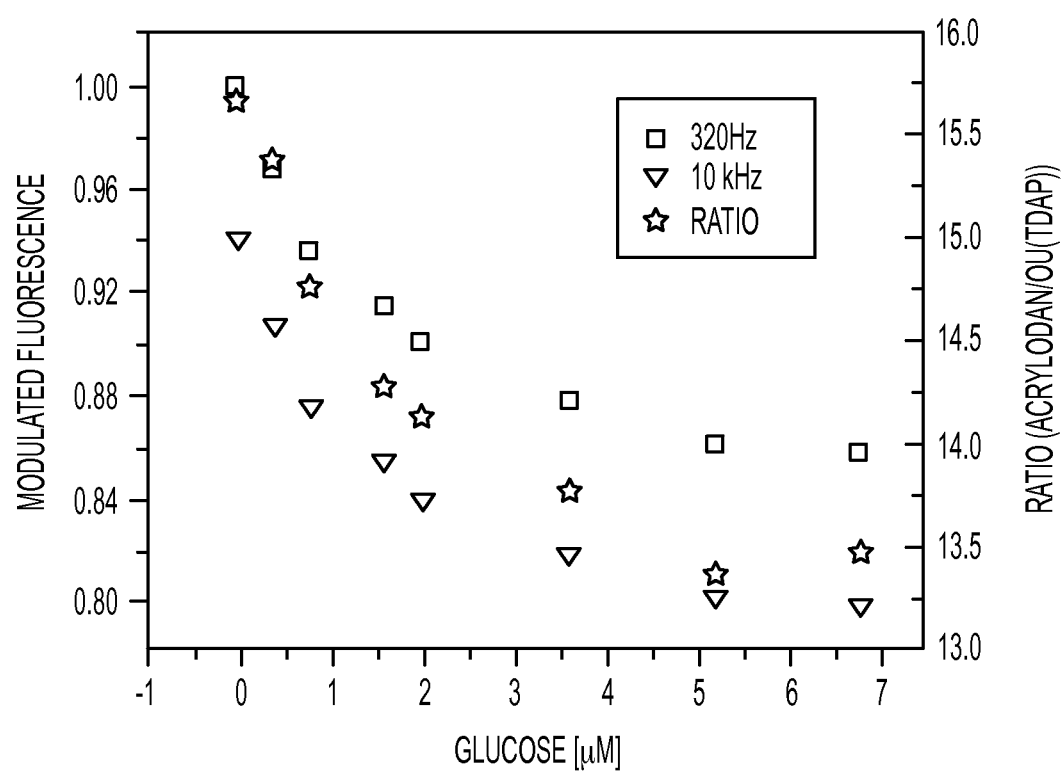
FIG. 11 is a plot showing GBP sensor response to intensity modulated excitation at two frequencies, as a function of glucose concentration.

FIG. 11 is a plot showing GBP sensor response to intensity modulated excitation at two frequencies, as a function of glucose concentration. The GBP sensor used europium as the reference dye, and the two excitation frequencies were 320 Hz and 10 KHz. The ratio of the emission at the two frequencies can be correlated to the analyte (glucose) concentration.

Figure 12:
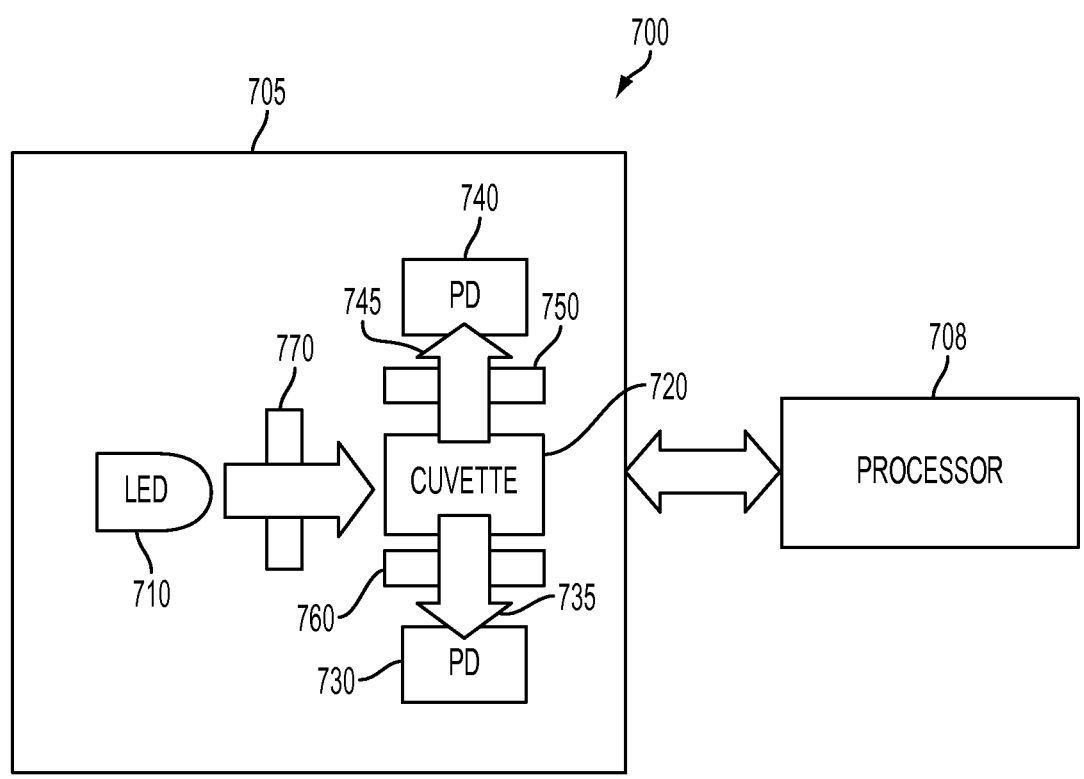
FIG. 12 is a schematic diagram of a glucose detection system that can be used to measure the glucose concentration in the glucose sample collected from the skin of a subject, in accordance with one embodiment of the present invention.

FIG. 12 is a schematic diagram of a glucose detection system 700 that can be used to measure the glucose concentration in the glucose sample collected from the skin of a subject, in accordance with one embodiment of the present invention. The glucose detection system 700 includes a fluorimeter 705 and a processor 708. The fluorimeter 705 includes an LED light source 710, a cuvette 720 for holding the GBP sensor and the glucose sample being analyzed, a first photodetector 730 for detecting the emission light 735 from the acrylodan fluorophore, and a second photodetector 740 for detecting emission light 745 from the reference fluorophore (either Eu or Ru).

The LED light source 710 is preferably a high-brightness LED having an emission maximum in the range of 390-400 nm for excitation of both fluorophores. Bandpass filters 750 and 760 are preferably used in front of the second and first photodetectors 740 and 730, respectively, for improving signal to noise. The acrylodan fluorophore has an emission maximum at approximately 520 nm, thus bandpass filter 760 is preferably a green bandpass filter, with the band centered at approximately 520 nm and a preferred bandwidth of approximately 40 nm.

The emission of Eu is centered at approximately 612 nm. Thus, if Eu is used as the reference fluorophore, then bandpass filter 750 is preferably a red bandpass filter that will pass 612 nm light with a preferred bandwidth of approximately 40 nm. The emission of Ru is centered at approximately 610-630 nm, depending on the type of Ru compound used. Thus, if Ru is used as the reference fluorophore, then bandpass filter 750 is preferably a red bandpass filter that will pass the emission light of the Ru compound being used with a preferred bandwidth of approximately 40 nm. Further, a bandpass filter or low pass filter 770 is used in front of LED light source 710 that will pass the excitation wavelengths of the acrylodan and reference fluorophores. The bandwidth of filter 770 is preferably 40-60 nm.

The fluorimeter 705 is controlled with the processor 708, which is suitably a computer running specialized software for displaying measurement results in real time and that is capable of storing data for future analysis. The software is also preferably adapted to extrapolate the blood glucose concentration in a subject based on the measurement results from the glucose sample obtained from the skin of the subject.

The processor 708 may be implemented with a general purpose desktop computer 200 or a general purpose laptop computer 210. In addition, the processor 120 may be implemented with a tablet computer 220 or smartphone 230, such as iOS, Android or Windows based tablets and smartphones. However, processor 708 can also be implemented with a special purpose computer, programmed microprocessor or microcontroller and peripheral integrated circuit elements, ASICs or other integrated circuits, hardwired electronic or logic circuits such as discrete element circuits, programmable logic devices such as FPGA, PLD, PLA or PAL or the like. In general, any device on which a finite state machine capable of executing code for implementing the functionality described herein can be used to implement the processor 708.

Figure 13:
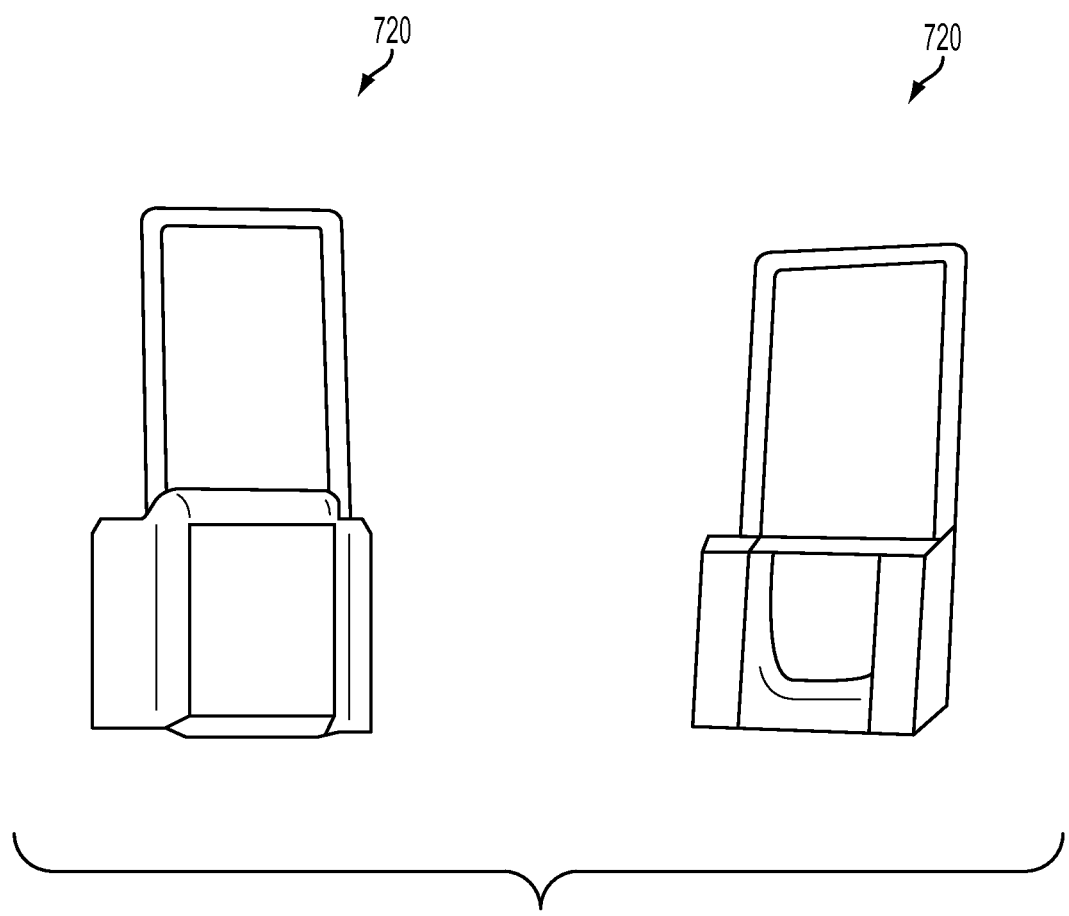
FIG. 13 is a perspective view of a preferred cuvette for use with the fluorimeter of FIGS. 12.

FIG. 13 is a perspective view of a preferred cuvette for use with the fluorimeter of FIG. 12. The cuvette preferably has a sample compartment thickness of approximately 1 mm and a sample volume of approximately 80 µL.

Figure 14:
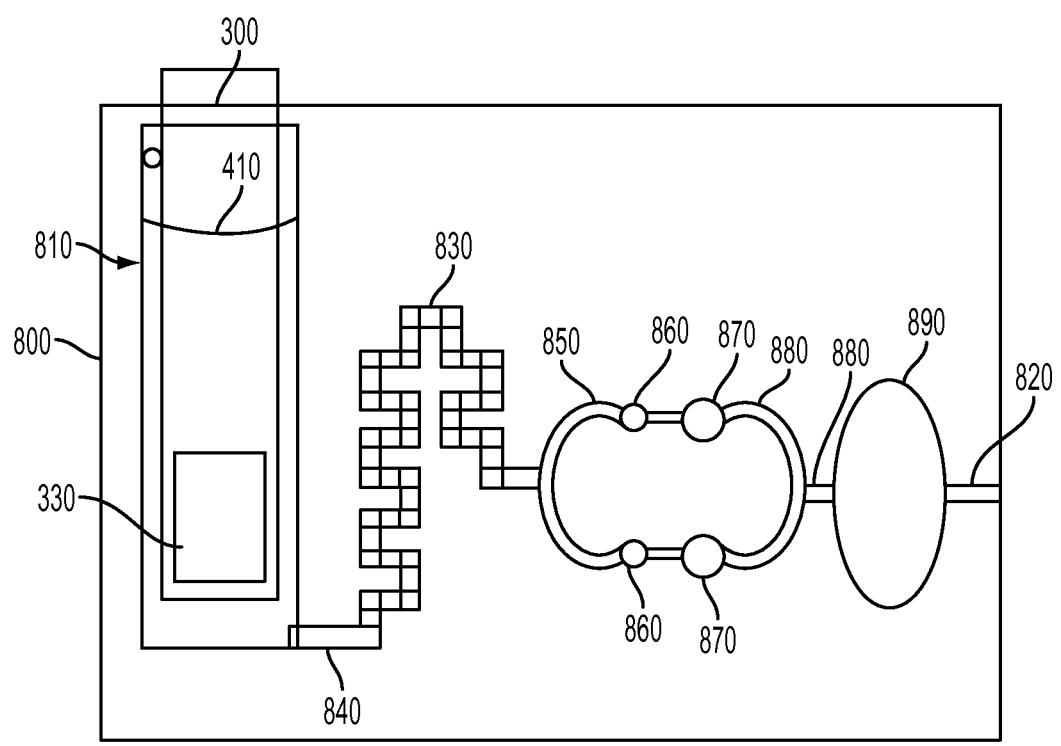
FIG. 14 is a schematic view of a microfluidic chip 800 that can be used in a handheld glucose sensor, in accordance with one embodiment of the present invention.

FIG. 14 is a schematic view of a microfluidic chip 800 that can be used in a handheld glucose sensor, in accordance with one embodiment of the present invention. The microfluidic chip 800 preferably incorporates a reservoir 810, similar to the reservoir 420 of FIGS. 5A and 5B for holding buffer solution 410 and for receiving the swab 300 that contains the filter paper 330 that has been exposed to skin glucose. In operation, the swab 300 is inserted into the reservoir 810 that contains buffer solution 410. Negative pressure is applied on port 820 with either a syringe (not shown) or with a small pump (not shown).

The negative pressure on port 820 will pull buffer solution 410 through mixing chambers 830, which are attached to the reservoir 810 via port 840. After passing through the mixing chambers 830, the buffer solution is split into two separate paths by splitter 850. The buffer solution 410 in each path goes through bubble traps 860 and into sensor wells 870, which contain GBP Sepharose beads. The bubble traps 860 are used to remove any air bubbles that may be present prior to entering the sensor wells 870.

The glucose in the buffer solution is then measured using a LARS-based fluorimeter. A fluorimeter similar to the fluorimeter 705 of FIG. 12 can be used, except that sensor wells 870 are used to hold the GBP sensor and buffer solution instead of the cuvette 720 shown in FIG. 12. After glucose measurements are completed, the buffer solution is pulled from the sensor wells 870 via waste path 880 and into waste reservoir 890.

The reservoir 420, mixing chambers 830, splitter 850, bubble traps 860, sensor wells 870, waste path 870, waste reservoir 890 and ports 820 and 840 are preferably made on a substrate that is transparent and that exhibits low fluorescence, suitably a poly(methyl methacrylate) substrate, a polystyrene substrate or cyclic polyofin substrate. The reservoir 420, mixing chambers 830, splitter 850, bubble traps 860, sensor wells 870, waste path 870, waste reservoir 890 and ports 820 and 840 can be manufactured on the substrate by etching, laser cutting or engraving, embossing injection molding or any other method known in the art.

Calibration of Methodology

A first preferred calibration method is to calibrate the glucose collection and measurement methodology for each subject based on the difference between an initial blood glucose measurement using conventional techniques (serum measurement) and a simultaneously collected skin measurement using one of the skin collection methods described above. A second preferred calibration method is to calibrate the glucose collection and measurement methodology based on average serum measurements and average skin measurements.

The first preferred calibration method performs better if there are moderate differences between subjects with regards to the bias of the glucose skin collection method. The second preferred calibration method performs better if the bias of the glucose skin collection method is similar between subjects, and if there is moderate measurement error in the skin collection results. Further, the second preferred calibration method exhibits two advantages: (1) clinically, it is much easier to implement by obviating the need to calibrate for each subject; and (2) the calibration adjustment can be modeled as a function of predictors of bias, such as, for infants, gestational age or postnatal age.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims. For example, although the present invention has been primarily described in connection with the noninvasive monitoring of blood glucose in infants by detecting and measuring glucose that has diffused through the skin and onto the skin surface, it should be appreciated that the present invention can be adapted to monitor the in vivo concentration of any type of small molecule substance by detecting and measuring the small molecule substance that has diffused through the skin. Further, the present invention can be used in adults, neonates or other mammals.

What is claimed is:

1. A method of determining blood glucose in a subject, comprising:
   placing a glucose collector in contact with an area of the skin of the subject, wherein the glucose collector is adapted to collect glucose that has passively diffused through the skin of the subject ("skin glucose");
   maintaining the glucose collector in contact with the skin area for a predetermined time that is sufficient to collect at least some of the skin glucose;
   measuring a concentration of the skin glucose collected by the glucose collector with a glucose detector that is adapted to measure the skin glucose collected by the glucose collector, wherein the glucose detector comprises a glucose binding protein sensor; and
   extrapolating blood glucose concentration in the subject based on a correlation between the blood glucose concentration in the subject and the measured skin glucose concentrations;
   wherein the glucose collector comprises a swab moistened with buffer solution, and wherein measuring a concentration of skin glucose on the swab with a glucose detector comprises, submerging the swab containing skin glucose in a buffer solution for a predetermined time that is sufficient to transfer at least some of the skin glucose from the swab to the buffer solution, placing the at least some of the skin glucose containing buffer solution in contact with the glucose binding protein sensor, measuring the fluorescence response of the glucose binding protein sensor after it has come into contact with the skin glucose containing buffer solution, and calculating a skin glucose concentration value based on the fluorescence response of the glucose binding protein sensor.

2. The method of claim 1, wherein the swab is pressed against the skin for the predetermined time.

3. The method of claim 1, further comprising washing the skin area for a predetermined period of time prior to placing the collector in contact with the skin area.

4. The method of claim 1, wherein the glucose binding protein sensor comprises a signal transducing fluorophore and a reference fluorophore.

5. The method of claim 4, wherein the glucose binding protein sensor is immobilized on Sepharose beads.

6. The method of claim 4, wherein the signal transducing fluorophore comprises acrylodan and the reference fluorophore comprises a ruthenium metal ligand complex or a europium metal ligand complex.

7. The method of claim 1, wherein the fluorescence response of the glucose binding protein sensor is determined with a fluorimeter.

8. The method of claim 7, wherein the fluorimeter is adapted to perform lifetime assisted ratiometric sensing.

9. The method of claim 1, wherein the swab comprises:
a housing;
a recess formed in the housing; and
a glucose absorbing material positioned in the recess such that when the swab is pressed against the skin the glucose absorbing material comes in contact with the skin.

10. The method of claim 9, wherein the housing comprises a pliable plastic housing.

11. The method of claim 1, wherein the swab containing skin glucose is submerged in buffer solution by placing the swab in a vessel that contains the buffer solution.

12. The method of claim 11, wherein the vessel comprises:
a reservoir for holding the buffer solution; and
a flexible septum attached to the reservoir and adapted to receive a syringe for withdrawing a sample of the buffer solution.

13. The method of claim 1, wherein the glucose detector comprises a microfluidic chip.

14. The method of claim 13, wherein the microfluidic chip comprises:
a substrate; and
a reservoir positioned on the substrate adapted to hold the buffer solution and to receive the swab such that the swab is immersed in the buffer solution;
at least one sensor well formed on the substrate that is fluidly coupled to the reservoir, wherein the sensor well is adapted to hold the glucose binding protein sensor.

15. The method of claim 14, wherein the glucose binding protein sensor comprises a signal transducing fluorophore and a reference fluorophore.

16. The method of claim 15, wherein the glucose binding protein sensor is immobilized on Sepharose beads.

* * * * *